United States Patent [19]

Chantler et al.

[11] Patent Number: 4,602,042
[45] Date of Patent: Jul. 22, 1986

[54] CONTRACEPTIVE METHODS

[75] Inventors: Eric N. Chantler, Stockport; Francis G. Hutchinson, Lymm; Deborah A. Sharman, Padfield, all of United Kingdom

[73] Assignee: Imperial Chemical Industries PLC, London, England

[21] Appl. No.: 638,641

[22] Filed: Aug. 7, 1984

[30] Foreign Application Priority Data

Oct. 14, 1983 [GB] United Kingdom ............... 8327561

[51] Int. Cl.$^4$ ............................................. A61K 31/155
[52] U.S. Cl. ............................................. 514/635; 514/843
[58] Field of Search ........................ 424/326; 514/635

[56] References Cited

U.S. PATENT DOCUMENTS 2,541,103  2/1951  Sander ............... 424/DIG. 14 X
4,424,216  1/1984  Cerami et al. .......... 424/211

FOREIGN PATENT DOCUMENTS 705838   1/1952  United Kingdom .
1095902  4/1965  United Kingdom .

OTHER PUBLICATIONS

Pineda et al, Theriogenology, 1981, vol. 16, pp. 1–11.
Pineda, Canine Practice, 1978, vol. 5, pp. 34–46.
Helgeland et al, Scand. J. Dent. Res., 1971, vol. 79, pp. 209–215.
Searl, Modern Veterinary Practice, 1979, vol. 60, pp. 504–506.
Pearson et al, The Veterinary Record, 1980, pp. 285–287.
Yu et al, British Journal of Urology, 1976, vol. 48, pp. 371–375.
Halim et al, British Medical Journal, 1973, Jul. 14, p. 110.

*Primary Examiner*—Leonard Schenkman
*Attorney, Agent, or Firm*—Cushman, Darby & Cushman

[57] ABSTRACT

This invention relates to the use of a bisbiguanide compound of the formula:

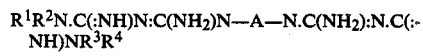

wherein either:
(i) $R^1$ and $R^3$, which may be the same or different, are each a phenyl radical which is substituted by alkyl, alkoxy, nitro or halogen, $R^2$ and $R^4$ are both hydrogen, and A is a 3–9C polymethylene diradical, wherein the polymethylene chain may be interrupted by oxygen atoms and/or by aromatic nuclei; or (ii) the bivalent bridge A is:
(a) alkylene of from 2 to 12 carbon atoms having the valence bonds attached to different carbon atoms,
(b) —(CH$_2$)$_m$—X—(CH$_2$)$_n$— wherein m an n each represent an integer from 2 to 6 and X is O or S,
(c)

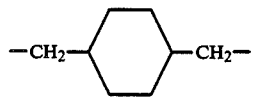

(d)

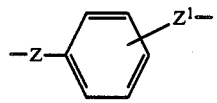

wherein Z and $Z^1$ are each alkylene of from 1 to 3 carbon atoms, (e)

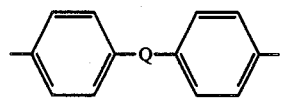

wherein Q is —O—, —S—, —SO— or —SO$_2$—, (f)

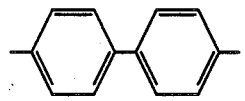

or

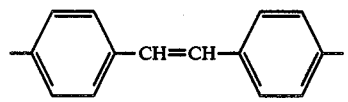

$R^1$ and $R^3$ are each:
(a) alkyl of from 6 to 16 carbon atoms, or
(b) alkyl-Y-alkylene, wherein Y is O or S and the alkyl and alkylene radicals together contain 3 to 15 carbon atoms;

and $R^2$ and $R^4$ are each hydrogen or 1–6C alkyl; or an acid addition salt thereof.

2 Claims, No Drawings

CONTRACEPTIVE METHODS

This invention relates to contraceptive methods, and in particular it relates to a method of increasing the viscosity of cervical mucus to such an extent as to render it essentially impermeable to sperm, and to a spermicidal or sperm-immobilising method.

Thus, according to the invention, there is provided a contraceptive method which comprises applying to the mucus in the vagina of a female mammal, a mucospissic amount of a bisbiguanide compound of the formula:

$$R^1R^2N.C(:NH)N:C(NH_2)N-A-N.C(NH_2):N.C(:NH)(NR^3R^4)$$   I wherein either:
(i) $R^1$ and $R^3$, which may be the same or different, are each a phenyl radical which is substituted by alkyl, alkoxy, nitro or halogen, $R^2$ and $R^4$ are both hydrogen, and A is a 3–9C polymethylene diradical, wherein the polymethylene chain may be interrupted by oxygen atoms and/or by aromatic nuclei; or
(ii) the bivalent bridge A is:
 (a) alkylene of from 2 to 12 carbon atoms having the valence bonds attached to different carbon atoms,
 (b) —(CH$_2$)$_m$—X—(CH$_2$)$_n$—wherein m and n each represent an integer from 2 to 6 and X is O or S,
 (c)

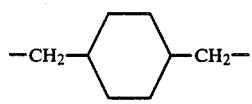

(d)

wherein Z and $Z^1$ are each alkylene of from 1 to 3 carbon atoms,
 (e)

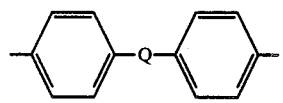

wherein Q is —O—, —S—, —SO— or —SO$_2$—,
 (f)

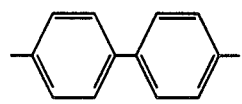

or

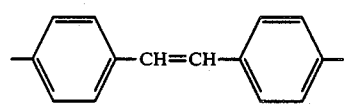

$R^1$ and $R^3$ are each:

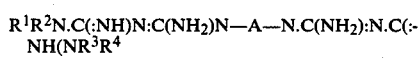

(a) alkyl of from 6 to 16 carbon atoms, or
(b) alkyl-Y-alkylene, wherein Y is O or S and the alkyl and alkylene radicals together contain 3 to 15 carbon atoms;
and $R^2$ and $R^4$ are each hydrogen or 1–6C alkyl;
or an acid addition salt thereof.

Bisbiguanide compounds of the formula I wherein the substituents have the values given in (i) are fully described in United Kingdom Pat. No. 705,838, and those wherein the substituents have the values given in (ii) are fully described in United Kingdom Pat. No. 1,095,902, and all the said compounds of the formula I are described as bactericides or plant fungicides.

Preferred bisbiguanide compounds of the formula I for use in the above method are chlorhexidine (I, $R^1=R^3=$p-chlorophenyl, $R^2=R^4=$hydrogen, $A=-(CH_2)_6-$) and the compound I, ($R^1=R^3=$2-ethylhexyl, $R^2=R^4=$hydrogen, $A=-(CH_2)_6-$) and their salts, especially the dihydrochlorides, diacetates and digluconates.

In this method, the compound of the formula I, when applied to the mucus at a suitable concentration, very rapidly increases its viscosity, to the extent that it becomes essentially impenetrable to sperm, and forms a physical barrier to conception in the same way as a rubber sheath or a diaphragm cap.

Besides increasing the viscosity of vaginal mucus, when the mucus comes into contact with a bisbiguanide compound of the formula I, other changes occur in its intrinsic properties, such as its morphology, rheology and water uptake and visco-elastic properties, which can also affect its penetrability to sperm.

In vitro, the compounds of the formula I exert a useful mucospissic effect at concentrations down to about $10^{-3}$ to $10^{-4}$%, and a suitable amount to be applied to the human vagina for contraceptive purposes is from 1.0 g. to $10^{-4}$ g.

According to a further feature of the invention there is provided a contraceptive method which comprises applying to the vagina of a female mammal a spermicidal or sperm-immobilising amount of a bisbiguanide compound of the formula I as defined above.

Preferred bisbiguanide compounds of the formula I for use in this aspect of the invention are chlorhexidine and the salts thereof, especially the dihydrochloride, diacetate and digluconate.

In vitro, the compound of the formula I exert their spermicidal or sperm-immobilising effect at a minimum concentration of $10^{-4}$ % w/v.

The compound of the formula I may be applied to the vagina in conventional manner, for example as a pessary, cream, liquid douche, gel, aerosol foam or impregnated tampon, or in a controlled delivery device of the compound in a polymer matrix.

According to a further feature of the invention there is provided a bisbiguanide compound of the formula I, or a composition thereof, for use as a contraceptive.

The mucospissic and sperm-immobilising properties of compounds of the formula I are demonstrated as in the following examples:

EXAMPLE 1

Chlorhexidine diacetate was dissolved in Tyrodes T6 balanced salt solution containing 4 mg./ml. of human albumin, and then mixed with an equal volume of bovine oestrous mucus. Mixing was achieved by four inversions of the tube containing the mixture, followed by 15 minutes standing to achieve equilibration. A sample of the mixture was then drawn by vacuum into capillary of rectangular section, 100 $\mu m \times 1.00$ mm $\times 5$ cm. One end of the filled capillary was then lowered into a reservoir containing human semen, with a sperm concentration of at least $50 \times 10^6$ per ml. and a motility of at least 80%. The system was incubated for 3 hours at 25° C. in an atmosphere saturated with water vapour, and the distance the leading sperm has then travelled along the capillary was measured by inspection under a microscope at about $200 \times$ magnification. The following results were obtained:

| Concentration of chlorhexidine (mg./ml.) | Mean distance travelled (mm.) | No. of assays |
| --- | --- | --- |
| 10.0 | 0 | 3 |
| 1.0 | 0 | 3 |
| 0.1 | 2.6 | 3 |
| 0.01 | 2.9 | 3 |
| 0.001 | 5.9 | 3 |
| 0.0(control) | 21.1 | 3 |

EXAMPLE 2

Chlorhexidine diacetate (50 $\mu$l. of an appropriate aqueous dilution) was dissolved in Tyrodes T6 balanced salt solution supplemented with 4 mg./ml. of human albumin, mixed with 50 $\mu$l. of fresh human semen with a sperm concentration of at least 50 million per ml. and a motility of at least 80%, and incubated at 25° C. for 3 minutes. The motility of the sperm so treated was measured by one of two methods:

(a) If the concentration of chlorhexidine caused protein precipitation, motility was estimated by phase contrast microscopy at $200 \times$ magnification in a 10 $\mu$m deep counting chamber.

(b) If the solution remained optically clear, motility was measured by laser Doppler spectroscopy. This technique involves the analysis by auto-correlation of the fraction of the scattered laser light which contains the Doppler-shifted frequencies generated by interaction between the incident laser and the sperm head.

The following results were obtained:

| Concentration of chlorhexidine (mg./ml.) | % of immotile sperm (control = 0) | No. of assays |
| --- | --- | --- |
| 1.0 | 95 | 4 |
| 0.1 | 71 | 4 |
| 0.01 | 54 | 4 |
| 0.001 | 41 | 4 |

EXAMPLE 3

Adult male and female Dutch rabbits were used. Only does exhibiting vaginal signs of oestrus were selected for treatment. Five does were treated with 2 ml. of chlorhexidine diacetate (1% in water) deposited at the cervix by means of a syringe fitted with a silastic cannula inserted into the upper vagina. Two hours after treatment the does were mated twice with a fertile buck. The does were killed 15 days later and the number of uterine implants and corpora lutea recorded. The following results are expressed as the percent inhibition in mean implant number, and egg loss, compared with a control group of 5 animals in which only 2 ml. of water was instilled.

| Group | Pregnant | Mean No. implants ($\pm$S.E.) | % Egg loss |
| --- | --- | --- | --- |
| Treated | 1/5 | $0.2 \pm 0.2$ | 98 |
| Control | 5/5 | $5.6 \pm .7$ | 24 |

EXAMPLE 4

The sperm-immobilising properties of chlorhexidine and compound 'A' (I,$R^1=R^3=$2-ethylhexyl, $R^2=R^4=$H) were compared with those of commercially used spermicidal agent nonoxynol 9, as follows.

Human semen, having a sperm count of greater than $20 \times 10^6$ per ml. and motility greater than 60%, (50 $\mu$l.) was mixed with a solution of the test compound (50 $\mu$l.) and a drop placed onto a Makler chamber. After 3 minutes, the number of immotile sperm was counted, and the percentage of sperm immobilised was calculated.

| % solution Compound | % of sperm immobilised | | | | | | | No. of replicates |
| --- | --- | --- | --- | --- | --- | --- | --- | --- |
| | $10^{-1}$ | $10^{-2}$ | $10^{-3}$ | $1^{-4}$ | $10^{-5}$ | $10^{-6}$ | $10^{-7}$ | |
| Chlorhexidine | 97 | 81 | 56 | 44 | 39 | 35 | 30 | 10 |
| Nonoxynol 9 | — | 44 | — | — | — | — | — | — |
| compound A | 100 | 72 | 22 | 26 | 12 | 9 | 7 | 15 |

EXAMPLE 5

The spermicidal effect of a test compound was determined as follows:

Human semen (200 $\mu$l.) and a 1.0% solution of the test compound in Tyrode's T6 medium with bovine serum albumin (BSA) added, were gently mixed. After 3 minutes, a further 1.0 ml. of the medium was added, and the mixture was centrifuged for 15 minutes at 415 g. The supernatant was removed, and the process repeated. The second pellet was resuspended in 1.0 ml. of the Tyrode's medium, and the motility of the sperm examined. Both chlorhexidine and nonoxynol irreversibly immobilised sperm, at this concentration, and are therefore spermicidal.

EXAMPLE 6

The mucospissic effects of chlorhexidine and nonoxynol 9 were compared as follows:

A solution of the test compound (50 $\mu$l) was mixed with bovine oestrus cervical mucus (100 $\mu$l) by repeated inversion, and the mixture was left for 15 minutes. The treated mucus was aspirated into a flat capillary tube (internal dimensions $0.1 \times 50$ mm.), one end of the tube was sealed with "Plasticine" and the other end was placed into a reservoir containing semen. The tube was placed in a petri dish containing damp tissue to maintain humidity and prevent the semen and mucus from drying. After 2 hours, the sperm penetration was assessed by counting the number of sperm per field under $100 \times$ magnification. The maximum distance penetrated by the sperm was determined, and the percentage reduction in penetration compared with a control was calculated.

| | 1. Distance penetrated (mm) | | | | | | | | |
|---|---|---|---|---|---|---|---|---|---|
| | Final concentration in mucus, % | | | | | | | | |
| Compound | 0.33 | $3.3 \times 10^{-2}$ | $3.3 \times 10^{-3}$ | $3.3 \times 10^{-4}$ | $3.3 \times 10^{-5}$ | $3.3 \times 10^{-6}$ | $3.3 \times 10^{-7}$ | $3.3 \times 10^{-8}$ | 0 (control) |
| Chlorhexidine | 0 | 0 | 0.6 | 0.6 | 1.2 | 3.6 | 11.2 | 17.1 | 26.5 |
| Nonoxynol 9 | 5.6 | 11.1 | 25.9 | — | — | — | — | — | 25.9 |

| | 2. % Reduction compared with control. | | | | | | | |
|---|---|---|---|---|---|---|---|---|
| | Final concentration in mucus, % | | | | | | | |
| Compound | 0.33 | $3.3 \times 10^{-2}$ | $3.3 \times 10^{-3}$ | $3.3 \times 10^{-4}$ | $3.3 \times 10^{-5}$ | $3.3 \times 10^{-6}$ | $3.3 \times 10^{-7}$ | $3.3 \times 10^{-8}$ |
| Chlorhexidine | 100 | 100 | 97.7 | 97.7 | 95.4 | 86.4 | 57.9 | 35.5 |
| Nonoxynol 9 | 78.6 | 57.1 | 0 | — | — | — | — | — |

EXAMPLE 7

The effect of the diffusion of test compounds into mucus on sperm penetration was determined as follows:

A capillary tube (internal dimensions $0.2 \times 0.2 \times 50$ mm.) was filled with bovine oestrus cervical mucus. A syringe was filled with a solution of the test compound, and connected by silicone tubing to one end of the flat capillary. At the other end of the capillary, semen was added either immediately (t=0) or at intervals (t=10,30 and 60 minutes) after the mucus had been first exposed to the test compound. The tube was left for 2 hours after the addition of semen, and the sperm penetration was assessed by counting the number of sperm per field at $100 \times$ magnification. A control tube was also assayed with Tyrode's T6 medium in place of the test solution. The maximum distance penetrated by sperm was determined, and the result expressed as % reduction compared with control, as follows:

| | | Contact time (minutes) | | | |
|---|---|---|---|---|---|
| Compound | % Solution | 0 | 10 | 30 | 60 |
| Chlorhexidine | 1.0 | 50 | 57 | 59.7 | 59.7 |
| | 0.5 | 66.8 | 66.8 | 71.5 | 76.3 |
| | 0.1 | 71.5 | 78.7 | 71.5 | 66.8 |
| | 0.01 | 66.4 | 64.4 | 66.8 | 66.8 |
| Nonoxynol 9 | 20.0 | 6.0 | 6.0 | 0.6 | 0 |
| | 10.0 | 6.0 | 6.0 | 0 | 0 |
| | 5.0 | 2.9 | 2.9 | 0 | 0 |
| | 1.0 | 6.0 | 0 | 0 | 0 |
| | 0.5 | 0 | 0 | 0 | 0 |

EXAMPLE 8

The procedure described in Example 3 was repeated, but the test treatment, and the interval between treatment and mating, were varied. The following results were obtained:

| Treatment | Treatment Mating Interval | Number pregnant | Mean ± SD No. of Implants | Egg loss |
|---|---|---|---|---|
| Water | 2 or 6 hrs | 19/19 | 7.7 ± 2.2 | 23/147 = 16% |
| Chlorhexidine 2 ml. × 1% | 2 hours | 3/14 | 0.5 ± 1.3 | 107/114 = 94% |
| Chlorhexidine 2 ml. × 1% | 6 hours | 4/10 | 0.8 ± 1.1 | 68/76 = 90% |
| Chlorhexidine 2 ml. × 1% | 24 hours | 5/10 | 3.3 ± 4.1 | 47/80 = 59% |
| Nonoxynol-9 2 ml. × 1% | 2 hours | 2/5 | 1.6 ± 2.3 | 35/43 = 81% |
| Nonoxynol-9 2 ml. × 1% | 6 hours | 5/6 | 3.3 ± 2.9 | 23/43 = 54% |
| *Nonoxynol-9 2 ml. × 5% in cream | 0 hours | 3/10 | 0.8 ± 1.9 | not given |
| *Nonoxynol-9 2 ml. × 5% in foam | 0 hours | 1/10 | 0.8 | not given |

*Data for Delfen Cream and Foam from Homm et al., Contraception, 13, 479, 1976).

What we claim is:
1. A contraceptive method which comprises applying to the mucus in the vagina of the female mammal, a mucospissic spermicidal or sperm-immobilizing amount of a bisbiguanide compound of the formula:

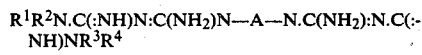

wherein either:
(i) $R^1$ and $R^3$, which may be the same or different, are each a phenyl radical which is substituted by alkyl, alkoxy, nitro or halogen, $R^2$ and $R^4$ are both hydrogen, and A is a 3-9C polymethylene diradical, wherein the polymethylene chain may be interrupted by aromatic nuclei; or
(ii) the bivalent bridge A is:
  (a) alkylene of from 2 to 12 carbon atoms having the valence bonds attached to different carbon atoms,
  (b) $-(CH_2)_m-X-(CH_2)_n-$ wherein m and n each represent an integer from 2 to 6 and X is O or S,
  (c)

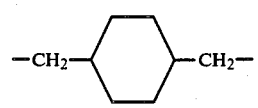

(d)

(e)

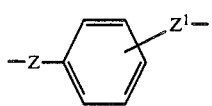

wherein Z and Z$^1$ are each alkylene of from 1, to 3 carbon atoms, (f)

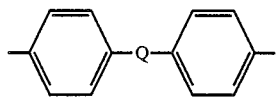

wherein Q is —O—, —S—, —SO— or —SO$_2$—,

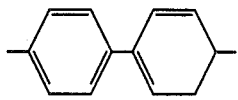

or

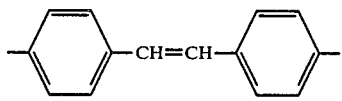

R$^1$ and R$^3$ are each:
(a) alkyl of from 6 to 16 carbon atoms, or
(b) alkyl-Y-alkylene, wherein Y is O or S and the alkyl and alkylene radicals together contain 3 to 15 carbon atoms; and R$^2$ and R$^4$ are each hydrogen or 1–6C alkyl;
or an acid addition salt thereof.

2. A method as claimed in claim 1 wherein the bisbiguanide compound is chlorhexidine or an acid addition salt thereof.

* * * * *